US006527752B1

(12) United States Patent
Bosley, Jr. et al.

(10) Patent No.: US 6,527,752 B1
(45) Date of Patent: Mar. 4, 2003

(54) EMBRYO TRANSFER CATHETER

(75) Inventors: Rodney W. Bosley, Jr., Bloomington, IN (US); Kathren J. Sips, Spender, IN (US)

(73) Assignee: Cook Urological, Inc., Spencer, IN (US)

( * ) Notice: Subject to any disclaimer, the term of this patent is extended or adjusted under 35 U.S.C. 154(b) by 32 days.

(21) Appl. No.: 09/669,315

(22) Filed: Sep. 25, 2000

Related U.S. Application Data

(60) Provisional application No. 60/156,049, filed on Sep. 24, 1999.

(51) Int. Cl.[7] ............................................. A16M 25/098
(52) U.S. Cl. ....................................... 604/264; 604/529
(58) Field of Search ................................. 604/264, 523, 604/529

(56) References Cited

U.S. PATENT DOCUMENTS

| | | |
|---|---|---|
| 4,401,124 A | 8/1983 | Guess et al. |
| 4,533,345 A | 8/1985 | Louw |
| 4,863,423 A | 9/1989 | Wallace |
| 4,877,033 A | 10/1989 | Seitz, Jr. |
| 5,081,997 A | 1/1992 | Bosley, Jr. et al. |
| 5,195,979 A * | 3/1993 | Schinkel et al. ........ 604/164.09 |
| 5,201,314 A | 4/1993 | Bosley et al. |
| 5,217,466 A * | 6/1993 | Hasson ........................ 604/27 |
| 5,259,837 A * | 11/1993 | Van Wormer ............... 600/435 |
| 5,273,527 A | 12/1993 | Schatz et al. |
| 5,289,831 A | 3/1994 | Bosley |
| 5,290,303 A | 3/1994 | Pingleton et al. |
| 5,486,191 A | 1/1996 | Pasricha et al. |
| 5,611,345 A | 3/1997 | Hibbeln |
| 5,724,977 A | 3/1998 | Yock et al. |
| 5,769,821 A | 6/1998 | Abrahamson et al. |
| 5,795,325 A | 8/1998 | Valley et al. |
| 5,843,023 A | 12/1998 | Cecchi |
| 6,036,682 A * | 3/2000 | Lange et al. ................. 604/264 |
| 6,302,875 B1 * | 10/2001 | Makower et al. ........... 604/528 |

FOREIGN PATENT DOCUMENTS

| | | |
|---|---|---|
| EP | 0456342 | 11/1991 |
| FR | 2272633 | 12/1975 |
| FR | 2635453 | 2/1990 |

\* cited by examiner

Primary Examiner—William E. Tapolcai
(74) Attorney, Agent, or Firm—James B. Hunt

(57) ABSTRACT

A cellular transfer catheter (10) is provided for implantation of cellular material into the uterus of a patient. The catheter includes a first component (11, 13) of a first material (26) which has a passageway (16) extending therethrough, and a second component (12) of a second material (27) having a higher durometer than the first material and suitable for assisting passage of the first component (11, 13) through a cervix and into the uterus of the patient. The first component (11, 13) includes a region (20) closely adjacent its distal end (18) having an ultrasonic reflectivity detectably different from the reflectivity of adjacent parts.

30 Claims, 3 Drawing Sheets

EMBRYO TRANSFER CATHETER

CROSS-REFERENCE TO RELATED APPLICATIONS

This application claims the benefit of U.S. Provisional Patent Application Ser. No. 60/156,049 filed Sep. 24, 1999.

TECHNICAL FIELD

This invention relates to medical devices, and more particularly to catheters used in minimally-invasive procedures.

BACKGROUND OF THE INVENTION

Human In Vitro Fertilization (IVF) and Embryo Transfer (ET), first successfully performed in 1978, has become a widely practiced procedure to treat infertile couples who have failed with more conventional methods of therapy such as superovulation and intrauterine insemination. The most common indications for IVF and related procedures, such as Gamete In Vitro Fertilization or Gamete Intra Fallopian Transfer (GIFT) which includes women having blocked or damaged fallopian tubes, and includes low sperm and/or egg quality. Related factors include age of the female, and the degree of endometrial receptivity. The procedure may also be used in cases of severe male factor where direct (intracytoplasmic) injection of sperm is an option. Another indication for the procedure is when the shell of the egg is abnormally thick, thus preventing the fertilized and dividing early embryo to escape and implant into the uterus. Creating a small opening through the shell has been shown to increase implantation rates. IVF is also being used when clinical or genetic factors require implantation of donor eggs from a fertile female that are fertilized in vitro and implanted into the recipient female using standard techniques.

The IVF/ET procedure typically involves the hormonal stimulation of the female to first suppress her ability to ovulate on her own, then stimulate development of follicles in the ovaries with a fertility medication. The mature eggs are removed from the ovary transvaginally using a needle, preferably guided under ultrasound. Following harvesting of the eggs, the eggs are identified and sorted with regard to maturity, and then placed with a sperm sample from the male. Approximately 24 hours after fertilization, the eggs are examined to confirm fertilization, which occurs in approximately 65% to 85% of the eggs harvested. After a short development period, the embryos are transferred, along with a volume of fluid, to the uterus using a delivery catheter. The delivery catheter is made of a soft plastic material to avoid damage to the endometrium. The delivery catheter is guided to the uterus by the physician who relies on an ultrasound probe to visualize the catheter.

While improvements in the techniques and instrumentation used in this procedure have provided significant increases in pregnancy rates and births, the overall numbers still remain fairly low. Recent numbers suggest an overall pregnancy rate of around 25% with a successful outcome rate of about 22%, these numbers being somewhat higher for younger patients. There are several factors that impact on the success of the procedure including some related to the design of the delivery catheter. The functions of the delivery catheter include serving as a housing for the embryos while the catheter is navigated to the implantation site; providing a relatively atraumatic extension from the stiffer guiding catheter for delivery; and serving as a conduit for injecting the fluid containing embryos into the endometrial cavity for implantation. Complications can include inadvertent flushing of the eggs into the fallopian tube, or suctioning the eggs out as the catheter is withdrawn. Visualization of the catheter can be another problem. Since ultrasound is two dimensional, the catheter can only be distinguished when it is relatively perpendicular with respect to the probe. When the catheter is angled, the reflected waves often do not return to the probe and visibility is lost. Because of the soft nature of the standard delivery catheter, in a number of cases, the tip of the catheter may bend back on itself or curve away from the fundus of the uterus. The tip may also accidently pass between the layer of the endometrium and myometrium. Misdirection of the catheter tip can be difficult to see under ultrasound and, if not corrected, usually results in lack of implantation and fertilization. Conversely, a stiffer catheter increases the risk of trauma to the uterus or cervix, with the latter possibly leading to the release of prostaglandins and expulsion of the eggs from the endometrium.

Another factor to be considered with respect to conventional IVF/ET procedures is that the cost of the procedure in conjunction with resulting relatively low pregnancy rates compels the delivery of multiple embryos during each procedure to increase the chance of at least one successful implantation. Often, unwanted multiple births result from this practice. If a higher pregnancy rate could be achieved, the need for multiple embryo implantation would be lessened or eliminated.

With the high cost of IVF and pregnancy rates that are still under 50%, what is needed is a soft-tipped catheter that can increase the likelihood of successful embryo implantation in a majority of the patients desiring this procedure. Ideally, the physician should be able to safely and accurately place the catheter at the implant site to deliver an optimal combination of fluid and embryos, resulting in successful implantation and birth of a healthy newborn.

SUMMARY OF THE INVENTION

The foregoing problems are solved and a technical advance is achieved in an illustrative transfer or delivery catheter which includes ultrasonically reflective components or features to enhance its visibility under transabdominal or transvaginal ultrasound guidance, during ET, for example. An exemplary embodiment of the invention includes coaxial catheter apparatus including an outer guide catheter and an inner transfer or delivery catheter. The guide catheter is preferably constructed of a relatively stiff material such as polytetrafluoroethylene (PTFE) and the transfer or delivery catheter is preferably constructed of a second material having a lower durometer such as polyethylene, urethane, polyolefin, amides, or silicone. The delivery catheter has a greater flexibility than the guide catheter, and that flexibility is achieved either by use of a lower durometer material or by shaping the delivery catheter so that it uses the same material as the guide catheter but is more flexible. In such a case, the external diameter of the delivery catheter will be less than that of the guide catheter. Ultrasonically detectable feature(s) is/are incorporated in the distal region of the transfer or delivery catheter, such as a band that is attached over the transfer or delivery catheter. The ultrasonically detectable feature or features may include, for example, an area or areas with reflectivity differing from that of the neighboring parts. The differing reflectivity may be greater or less than that of the neighboring parts. Ultrasonically detectable feature or features may also be incorporated adjacent the distal tip of the guiding catheter.

The catheter apparatus may alternately comprise a single piece comprising a stiffened proximal component or portion or a reinforcement component or member, as an outer or inner tube or cannula Where the catheter is used for embryo transfer, the diameter of the passageway through the transfer catheter is preferably no greater than 0.025", and most preferably between 0.018" and 0.021". Such a diameter would permit a transfer volume (the volume of fluid and material including at least one gamete, blastocyst or zygote) less than 30 µl and most preferably between 5 and 15 µl.

BRIEF DESCRIPTION OF THE DRAWINGS

Embodiments of the invention will now be described by way of example with reference to the accompanying drawings, in which.

DETAILED DESCRIPTION

Figure 1:
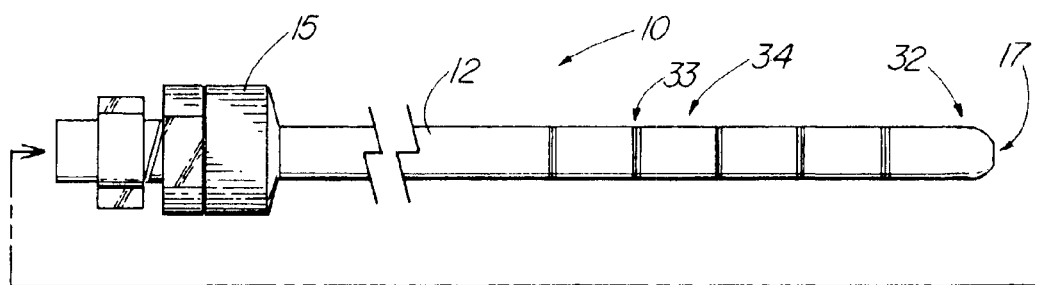
FIG. 1 depicts a partially sectioned side view, with enlargement, of the catheter of the present invention.
Figure 1:
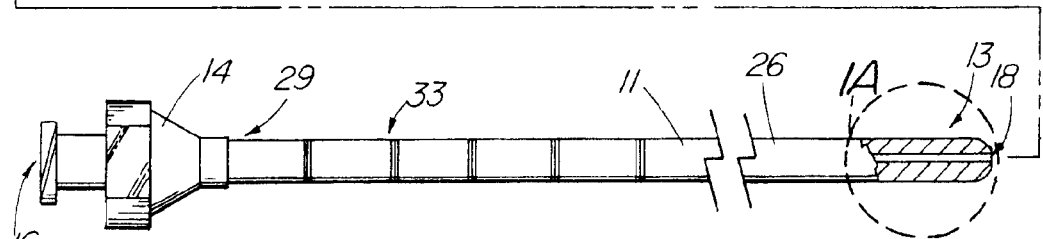

FIGS. 1–9 depict a coaxial embryo transfer catheter 10 of the present invention comprising two components 11, 12 preferably of differing stiffness with the first component 11 extending beyond the distal end of the second component. The first component 11 includes a passageway 16 of sufficient diameter to hold and deliver early embryos, gametes (oocyte or sperm), blastocysts, or zygotes that are to be transferred from in vitro culture for in vivo implantation and/or fertilization. The diameter of the passageway and volume of the fluid and material contained therein is preferably minimized to a diameter of no greater than 0.025", preferably less than 0.023", and most preferably between 0.018" and 0.021". By way of comparison, the diameter of the lumen in the similar Soft-Pass™ Catheter is approximately 0.026". As a result, the Soft-Pass™ Catheter (Cook OB/GYN, Spencer, Ind.) has a transfer volume (the volume of fluid and material including at least one gamete, blastocyst or zygote) of 30 to 50 µl, while in the present invention, the transfer volume is no greater than 30 µl, more preferably 20 µl or less, and most preferably between 5 and 15 µl. Clinical experience with this catheter for IVF/ET having a 0.020" diameter with a volume of approximately 10 µl indicates an unexpected increase in pregnancy rates, possibly due to the reduced amount of fluid delivered with the embryos. The reduced transfer volume ostensibly lessens the tendency of embryos to migrate to another section of the uterus, for instance, into the fallopian tubes. By increasing the implantation rate, fewer embryos may be needed, thereby reducing the number of unwanted multiple pregnancies with the attendant risks. FIG. 1 depicts a embryo transfer catheter in which the first and second components 11, 12 comprise an inner delivery catheter 11 made of a first material 26 preferably having a low durometer, such as polyethylene, urethane, polyolefin, amides, or silicone; and an outer guiding catheter 12 of a second material preferably having a higher durometer such as polytetrafluoroethylene (PTFE). In addition, any material herein can be chosen depending on the modulus of elasticity of the material. The same list of materials for the delivery catheter can also be used to make the guiding catheter, however, it would be advantageous to increase the durometer or add stiffness to the guiding catheter by another means. It should be noted that PTFE can be used to make the delivery catheter, despite the relative stiffness of the material.

The illustrative embodiment of cellular transfer catheter 10 is used coaxially. The outer guiding catheter 12 has a passageway 17 into which the delivery catheter 11 is inserted. The guiding catheter 12 offers the required stiffness for navigating the transfer catheter 10 through the endocervix and into the endometrial cavity. The delivery catheter 11 is inserted through the guiding catheter 12, either prior to, or after, introduction of the device into the endometrial cavity. In the illustrative embodiment the delivery catheter 11 and guiding catheter 12 each have a proximal hub 14, 15 with the delivery catheter hub 14 fitting inside the guiding catheter hub 15 during use of the device 10. When inserted prior to the procedure, the delivery catheter offers a softer tip to reduce the risk of damaging the cervical or uterine tissues. In the illustrative embodiment, the guiding catheter has an outer diameter of 6.8 Fr and an overall length of about 17 cm. The inner catheter diameter is 4.4 Fr with a length of approximately 32.5 cm. The delivery catheter extends approximately 5 cm beyond the tip of the guiding catheter. Optional graduated markings 33 can be placed about the proximal portion 29 of the delivery catheter 11 and/or the distal portion 34 of the guiding catheter to determine the depth of penetration into the uterus or the amount of delivery catheter 11 that is exposed beyond the distal tip 32 of the guiding catheter 12.

Figure 5:
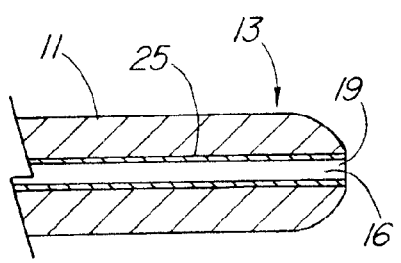
FIG. 5 depicts a cross-sectional view of a fourth alternative embodiment of the present invention.

Because the delivery catheter is preferably made of a softer (low durometer) polymer the surface energy density is usually higher, making the embryo more likely to adhere to the inner luminal surface 19. This is especially critical with the reduced lumen diameter since with a typical oocyte having a diameter of about 100 microns and a blastocyst, a diameter of about 130 microns, there is an increased likelihood of problems in delivery. Luminal surface treatments may help reduce friction for the smooth expulsion of oocytes and embryos. Ion beam bombardment is a well-known technique for reducing surface energy density of polymers. Polishing and surface coatings can also offer improvement in friction coefficients for otherwise "sticky" polymers. FIG. 5 depicts an embodiment in which the luminal surface 19 of the passageway 16 of the delivery catheter is coated with lubricious material, such as parylene, to reduce surface energy density.

Figure 2:
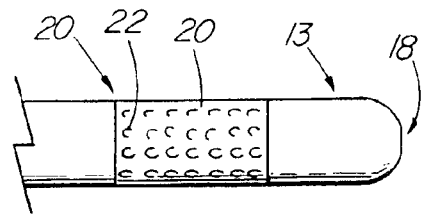
FIG. 2 depicts an enlarged side view of an alternative embodiment of the present invention.
Figure 1A:
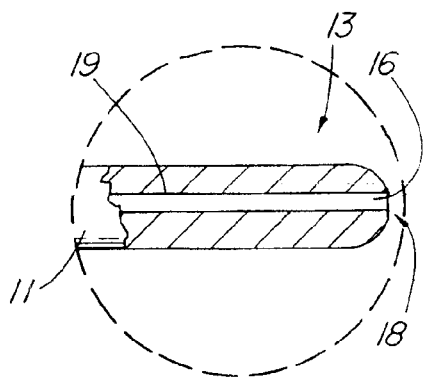
Figure 3:
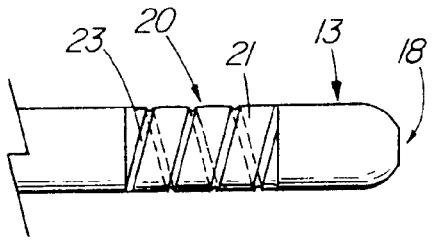
FIG. 3 depicts an enlarged side view of a second alternative embodiment of the present invention.
Figure 4:
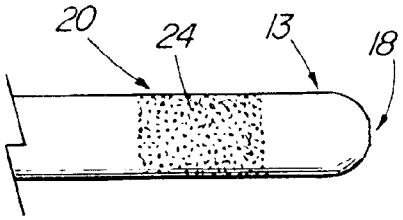
FIG. 4 depicts an enlarged side view of a third alternative embodiment of the present invention.

FIGS. 2–4 depict alternative embodiments of the present invention having ultrasonically reflective components or features 20 to enhance visibility under transabdominal or transvaginal ultrasound guidance during ET. In the embodiments of FIGS. 2–3, the ultrasonically reflective features 20 comprise a third material such as a band 21 that is attached over the delivery catheter 11, preferably 2–3 mm from the distal tip 18. The band 21 may be a simple cylindrical metallic band whose edges would tend to scatter back ultrasound, but inclusion of additional ultrasonically reflective features increases its effectiveness. In the embodiment of FIG. 2, the ultrasonically reflective features include a plurality of indentations 22 that are preferably semi-spherical or semi-circular in shape. This, and related embodiments of ultrasonically reflective features 20, are described in U.S. Pat. No. 5,289,831 to Bosley and U.S. Pat. No. 5,081,997 to Bosley, Jr. et al., the disclosures of which are hereby expressly incorporated by reference. In the embodiment of FIG. 3, the band 21 includes a diffraction gradient 23, such as grooves (as shown), bars, lines, or bands on the surface of the band 21 to reflect or scatter ultrasound waves that would otherwise deflect away from the smooth surface of the catheter. This type of reflecting means is the subject of U.S. Pat. No. 4,401,124 to Guess et al., the disclosure of which is also hereby expressly incorporated by reference.

The band 21, which should be no larger in diameter than the delivery catheter, can be attached by any of a number of methods. In a first method, the distal portion 13 of the delivery catheter is stepped down in diameter such that the band 21 can be slid over to abut with the proximal portion of the catheter having the nominal diameter. The portion of the delivery catheter 11 distal to the band 21 is then heated and reformed to the nominal diameter, thereby creating a recessed area in which the band resides. A second method involves having the distal portion 13 of the delivery catheter be of a higher durometer than the proximal portion 29. The proximal portion is stepped down for receiving the band 21, then is reformed to retain the band 21 proximate to the distal tip 18 of the catheter. A third method of attaching the tip includes resiliently stretching the distal portion 13 of the catheter to reduce the diameter and inserting the band over the catheter. The catheter tends to return to the original diameter. The catheter distal tip 18 is then rounded and the band is secured to the catheter using an adhesive.

FIG. 4 depicts an embodiment whereby the ultrasonically reflective features 20 comprise particles 24, usually spherically shaped, that are bonded to, or incorporated into, the outer surface of the catheter to scatter and reflect incident ultrasound energy to increase visibility of the tip. This embodiment is also described in the Bosley patents, mentioned supra.

Figure 6:
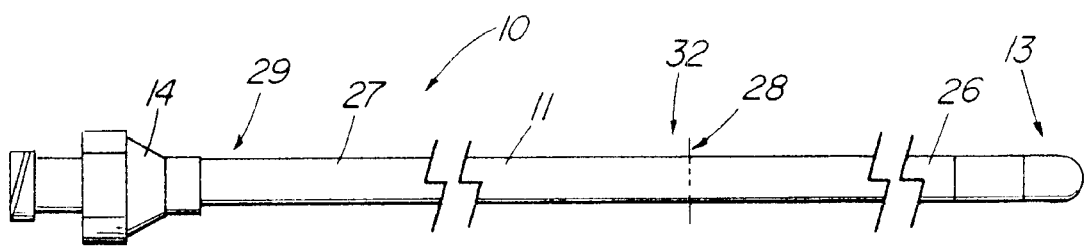
FIG. 6 depicts a side view of a fifth alternative embodiment of the present invention.
Figure 7:
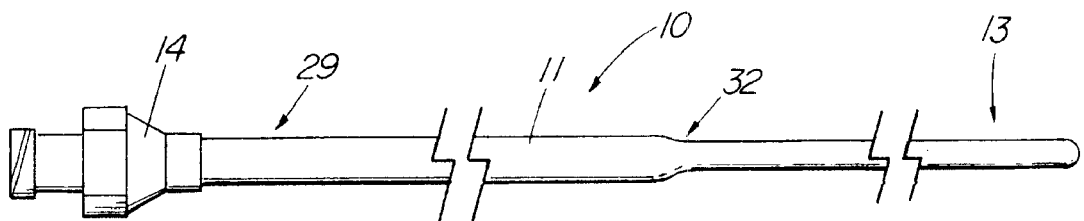
FIG. 7 depicts a side view of a sixth alternative embodiment of the present invention.
Figure 8:
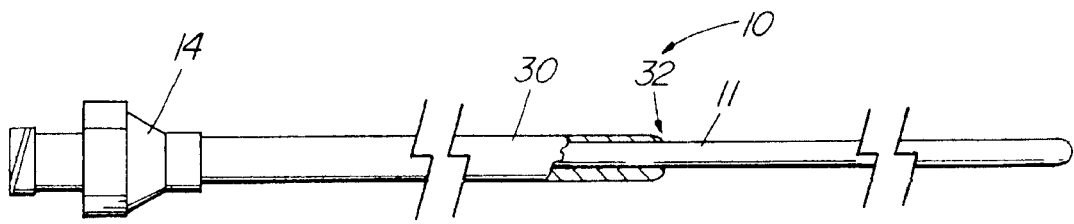
FIG. 8 depicts a side view of a seventh alternative embodiment of the present invention.
Figure 10:
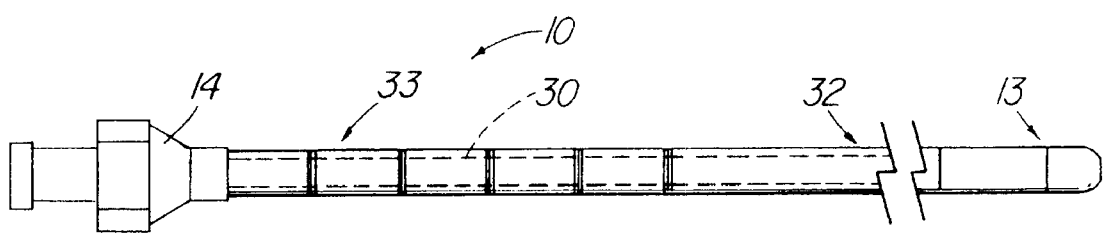
FIG. 10 depicts a side view of a ninth alternative embodiment of the present invention.

In addition to the coaxial catheter arrangement as depicted in FIG. 1, the embryo transfer catheter 10 can be made as a single piece comprising the delivery catheter 11 with a stiffened proximal component or portion 29 (as depicted in FIGS. 6 and 7), or a reinforcement component or member 30, as an outer tube or cannula, depicted in FIG. 8, or inner tube or cannula, depicted in FIG. 10, that is preferably connected with the delivery catheter at the single proximal hub 14 and/or bonded to the delivery catheter by heat or adhesive. Where an inner cannula is used as depicted in FIG. 10, an example of material which might be used comprises a polyolefin tubing having a passageway 16 of 4.4 Fr diameter in combination with a cannula of 23GXTW stainless steel. It is not required that the two tubes 11, 30 be bonded along their length. The coaxial embryo transfer catheter 11, depicted in FIG. 1, provides the ability to shorten the exposed length of the soft distal portion 13 of the delivery catheter 11 in difficult cases, when necessary. Since this usually only occurs in less than 10% of the cases, a single-piece embryo transfer catheter 10 with sufficient stiffness for navigation may also be used successfully in most instances.

Referring now to the embodiment of FIG. 6, the embryo transfer catheter 10 preferably comprises two different materials or durometers of the same material. The distal portion 13, comprising the softer material, is bonded to the stiffer proximal portion 29 at a joint or interface 28. An alternative method of fabricating the embodiment of FIG. 6 is to coextrude two different polymers with the interface 28 comprising a zone of transition between the different materials. FIG. 7 depicts a single-piece embryo transfer catheter 10 made of a single material stepped down in diameter from the proximal portion 29, to the smaller-diameter (and thus more flexible) distal portion 13.

Figure 11:
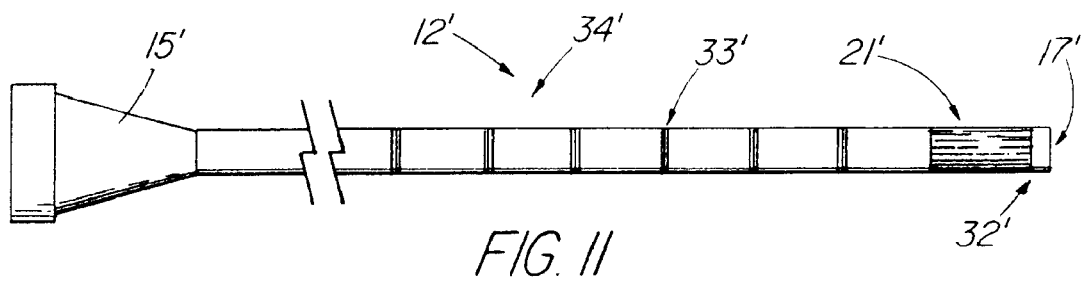
FIG. 11 depicts a side view of an alternative embodiment of a guide catheter for use with the delivery catheter of FIG. 1.

Referring now to FIG. 11, it may also be desirable to include ultrasonically reflective features of the type described herein, such as the band 21' shown, adjacent the distal tip 32' of the guiding catheter 12' so that the location of the guiding catheter 12' may be detected ultrasonically. The guiding catheter 12' of FIG. 11 is of an alternate configuration wherein a proximal hub 15' shaped is bonded to a polyethylene tube having an inner passage 17' graduated markings 33' are preferably provided at the distal portion 34' of the guiding catheter 12' to visually determine the depth of penetration into the uterus or the amount of delivery catheter 11 that is exposed beyond a distal tip 32' of the guiding catheter 12'. As with the regions described for use on the delivery catheter of FIGS. 1–10, any suitable method may be employed which presents a region of ultrasonic reflectivity different from the ultrasonic reflectivity of adjacent parts.

Figure 9:
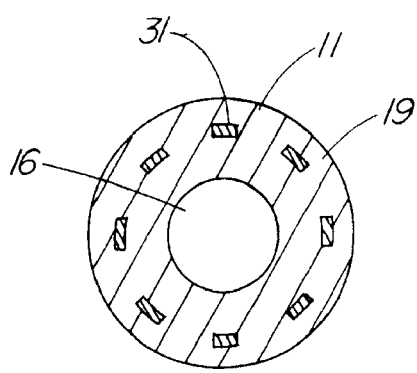
FIG. 9 depicts a cross-sectional view of an eighth alternative embodiment of the present invention.

To provide additional reinforcement to the proximal portion 29 of the delivery catheter 11, either directly, or via the outer catheter 12 or reinforcement member 30, reinforcement strands 31, such as wire braiding, can be incorporated into the walls 19 of the tube using well-known methods. FIG. 9 depicts a cross-sectional view of the proximal portion 29 of a delivery catheter 11 in which a wire braid 31 is melted or layered into the delivery catheter 11 to obviate the need for a stiffening guide catheter.

The details of the construction or composition of the various elements of the cellular transfer catheter not otherwise disclosed are not believed to be critical to the achievement of the advantages of the present invention, so long as the elements possess the strength or flexibility or softness needed for them to perform as disclosed. The selection of such details of construction is believed to be well within the ability of one of even rudimentary skills in this area, in view of the present disclosure, and are within the spirit of the invention and the scope of the claims.

What is claimed is:

1. A cellular transfer catheter for implantation of cellular material into the uterus of a patient, the cellular transfer catheter (10) comprising:

a first component (11, 13), the first component (11) having a distal end (18) and a passageway (16) extending therethrough; and a second component (12, 29, 30) having a greater stiffness than the first component and suitable for assisting passage of the first component (11) through a cervix and into the uterus of the patient;

said first component (11) including a region (20) closely adjacent its distal end (18) having an ultrasonic reflectivity detectable different from the reflectivity of adjacent parts.

2. The catheter (10) of claim 1, wherein the passageway (16) has an inner diameter no greater than 0.025".

3. The catheter of claim 2, wherein the inner diameter of the passageway (16) is less than 0.023".

4. The catheter of claim 3, wherein the inner diameter of the passageway (16) is between 0.018" and 0.021".

5. The catheter of claim 1, wherein the region (20) has an outer surface having indentations (22, 23) therein.

6. The catheter of claim 5, wherein at least a portion of the indentations (22, 23) are semicircular in shape.

7. The catheter of claim 1, wherein the region (20) comprises a third material.

8. The catheter of claim 7, wherein the region (20) comprises a metallic band (21) affixed proximate to the distal end (18) of the first component (11).

9. The catheter of claim 7, wherein the third material comprises discrete elements (24) embedded within one of the region (20) and the second material (26), of the first component (11, 13).

10. The catheter (10) of claim 1, wherein the first component comprises a first material (26) and the second component comprises a second material (27) having a higher durometer than the first material.

11. The catheter of claim 1 wherein the second component includes a further region closely adjacent its distal end, the further region having an ultrasonic reflectivity detectable different from the reflectivity of adjacent parts.

12. The catheter of claim 11 wherein the second component comprises graduated markings at its distal end.

13. The catheter of claim 1 wherein the region has a greater ultrasonic reflectivity than adjacent parts.

14. The catheter of claim 1 wherein the first component and the second component are formed as a single piece.

15. The catheter of claim 1 wherein the first component comprises graduated markings at its proximal end.

16. The catheter of claim 15 wherein the second component comprises graduated markings at its distal end.

17. The catheter of claim 13 wherein the second component comprises a stiffened proximal portion.

18. The catheter of claim 13 wherein the stiffened proximal portion comprises a tube surrounding the second component.

19. The catheter of claim 13 wherein the stiffened proximal portion comprises an inner tube disposed within the second component.

20. A cellular transfer cathether (10) comprising:

an outer member (12) that comprises a first material (26), the outer member (12) having a passage (17) therethrough; and an inner member (11) slidably disposed within the outer member (12), the inner member (11) comprising a second material (27) having a lower durometer and greater flexibility than the first material (26), the inner member (11) having a passageway (16) therethough;

said inner member (11) further including a region (20) having an outer surface, the region (20) disposed closely adjacent the distal end (13) of the inner member (11), the region (20) further comprising an ultrasonically reflective component (21, 24).

21. The catheter of claim 20, wherein the passageway (16) has an inner diameter no greater than 0.025".

22. The catheter of claim 11, wherein the inner diameter of the passageway (16) is less than 0.023".

23. The catheter of claim 22, wherein the inner diameter of the passageway (16) is between 0.018" and 0.021".

24. The catheter of claim 20, wherein the ultrasonically reflective component (21, 24) comprises indentations (22, 23) in the outer surface of the region (20).

25. The catheter of claim 24, wherein at least a portion of the indentations (22, 23) are semicircular in shape.

26. The catheter of claim 20, wherein the ultrasonically reflective component (21, 24) comprises a third material.

27. The catheter of claim 26, wherein the region (20) comprises a metallic band (21) affixed proximate to a distal tip (18) of the inner member (11).

28. The catheter of claim 26, wherein the third material comprises discrete elements (24) embedded within one of the region (13) and the second material (26), of the inner member (11).

29. A cellular transfer catheter (10) comprising:

an outer member (12) that comprises a first material (26), the outer member (12) having a passageway (16) therethrough;

an inner member (11) slidably disposed within the outer member (12), the inner member substantially comprising a second material (27) having a lower durometer and greater modulus of elasticity than the first material (26), the inner member (11) having a passageway (16) extending therethough, the passageway (16) having an inner diameter between 0.018" and 0.021" for permitting a transfer volume between 5 $\mu l$ and 15 $\mu l$;

a region (20) having an outer surface disposed about the distal end (13) of the inner member (11), the region (20) including semicircular-shaped indentations in its outer surface.

30. The catheter of claim 29, wherein the region (20) comprises a metallic band (21) disposed about the distal end (13) of the inner member (11).

* * * * *